United States Patent [19]

Schneider et al.

[11] 4,096,195
[45] Jun. 20, 1978

[54] CYCLIC TWO-STAGE NITRATION PROCESS FOR PREPARING 4-CHLORO-3,5-DINITROBENZOTRIFLUORIDE FROM 4-CHLOROBENZOTRIFLUORIDE

[75] Inventors: Louis Schneider, Elizabeth; David E. Graham, Westfield, both of N.J.

[73] Assignee: GAF Corporation, New York, N.Y.

[21] Appl. No.: 796,519

[22] Filed: May 13, 1977

[51] Int. Cl.$^2$ ............................................. C07C 79/12
[52] U.S. Cl. .................................................. 260/646
[58] Field of Search ........................................ 260/646

[56] References Cited

U.S. PATENT DOCUMENTS

| 2,257,093 | 9/1941 | Friedrich et al. | 260/646 |
| 3,726,930 | 4/1973 | Smith et al. | 260/646 |

FOREIGN PATENT DOCUMENTS

| 197,612 | 7/1967 | U.S.S.R. | 260/646 |

*Primary Examiner*—Leland A. Sebastian
*Attorney, Agent, or Firm*—Walter C. Kehm; Walter Katz

[57] ABSTRACT

In accordance with the present invention, there is provided herein a cyclic, two-stage process for dinitrating 4-chlorobenzotrifluoride to form 4-chloro-3,5-dinitrobenzotrifluoride in high yield. The process commences with a mononitration stage wherein 4-chlorobenzotrifluoride is substantially completely converted to 4-chloro-3-nitrobenzotrifluoride (the "monoitro" compound) in the presence of a nitric acid, sulfur trioxide and sulfuric acid mixture. The used acid mixture then is diluted with water to form an aqueous used acid layer in which the solubility of the mononitro compound is negligible and a mononitro layer. The aqueous used acid layer then is separated from the mononitro layer and discarded. The mononitro compound thereafter is further nitrated in a dinitration stage in the presence of a fresh nitric acid, sulfur trioxide and sulfuric acid mixture. The fresh acid mixture contains an excess of nitric acid sufficient to carry out both nitrations using the partially spent acid mixture of the dinitration stage as the acid mixture for the mononitration stage. The reaction product of the dinitration stage is the desired dinitro compound and a partially spent acid mixture, which contains some dinitro compound dissolved therein. The dinitro layer then is separated from the partially spent acid layer and recovered and the acid layer is recycled back to the mononitration stage.

14 Claims, 1 Drawing Figure

MONONITRATION STAGE              DINITRATION STAGE

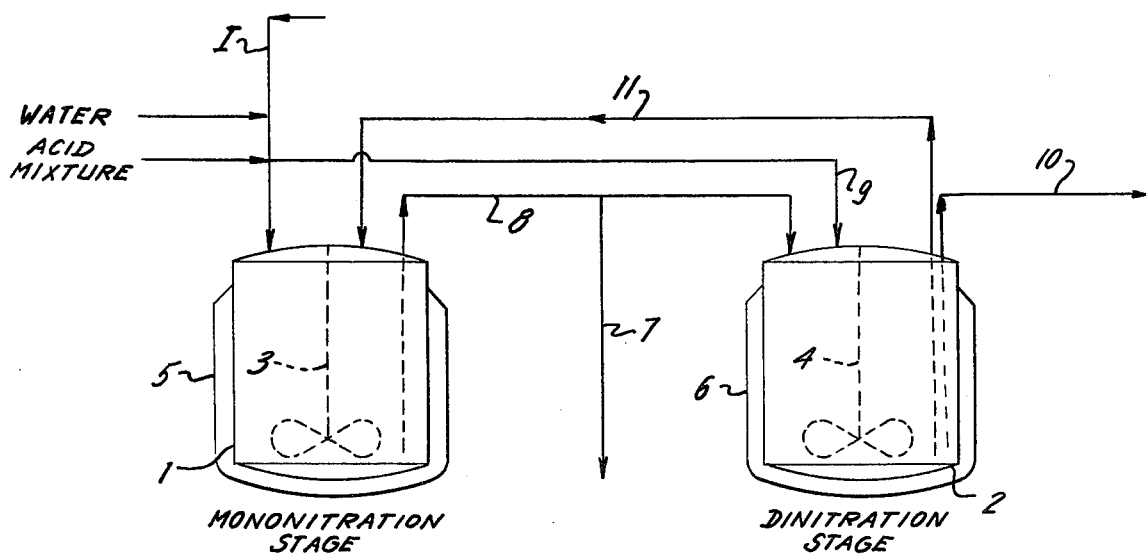

CYCLIC TWO-STAGE NITRATION PROCESS FOR PREPARING 4-CHLORO-3,5-DINITROBENZOTRIFLUORIDE FROM 4-CHLOROBENZOTRIFLUORIDE

BACKGROUND OF THE INVENTION

1. Field of the Invention

This invention relates to the dinitration of 4-chlorobenzotrifluoride to form 4-chloro-3,5-dinitrobenzotrifluoride, and, more particularly, it is concerned with a cyclic, two-stage nitration process for obtaining the desired compound in high yield.

2. Utility of the Invention 4-chloro-3,5-dinitrobenzotrifluoride (the "dinitro" compound) is an important intermediate in the preparation of N-(2-chloroethyl)-2,6-dinitro-N-propyl-4-trifluoromethylaniline, a herbicidally active agricultural chemical. Accordingly, it is desired to provide new and improved methods of preparing this intermediate, preferably from the available 4-chlorobenzotrifluoride precursor.

3. Description of the Prior Art

Many methods are known in the art to nitrate organic compounds. However, in order to be suitable for use commercially, a given nitration process must provide the desired nitro compound in high yield, selectively, that is, without an excessive amount of undesirable by-products, and within a reasonable reaction period. Accordingly, it is an object of the present invention to provide such a commercial process, wherein 4-chlorobenzotrifluoride is efficiently and selectively converted into 4-chloro-3,5-dinitrobenzotrifluoride, and the product is isolated in high yield within a short time cycle.

SUMMARY OF THE INVENTION

In accordance with the present invention, there is provided herein a cyclic, two-stage process for dinitrating 4-chlorobenzotrifluoride to form 4-chloro-3,5-dinitrobenzotrifluoride in high yield. The process commences with a mononitration stage wherein 4-chlorobenzotrifluoride is substantially completely converted to 4-chloro-3-nitrobenzotrifluoride (the "mononitro" compound) in the presence of a nitric acid, sulfur trioxide and sulfuric acid mixture. The used acid mixture then is diluted with water to form an aqueous used acid layer in which the solubility of the mononitro compound is negligible and a mononitro layer. The aqueous used acid layer then is separated from the mononitro layer and discarded. The mononitro compound thereafter is further nitrated in a dinitration stage in the presence of a fresh nitric acid, sulfurtrioxide and sulfuric acid mixture. The fresh acid mixture contains an excess of nitric acid sufficient to carry out both nitrations using the partially spent acid mixture of the dinitration stage as the acid mixture for the mononitration stage. The reaction product of the dinitration edge is the desired dinitro compound and a partially spent acid mixture, which contains some dinitro compound dissolved therein. The dinitro layer then is separated from the partially spent acid layer and recovered and the acid layer is recycled back to the mononitration stage.

DETAILED DESCRIPTION OF THE INVENTION

In the Drawings

The FIGURE is a schematic illustration of the cyclic, two-stage nitration process for the production of 4-chloro-3,5-dinitrobenzotrifluoride in accordance with the teachings of the invention.

DESCRIPTION OF THE PREFERRED EMBODIMENTS

1. General Conditions of the Process

The nitration process, per se, proceeds in two stages, a mononitration stage and a dinitration stage, as follows:

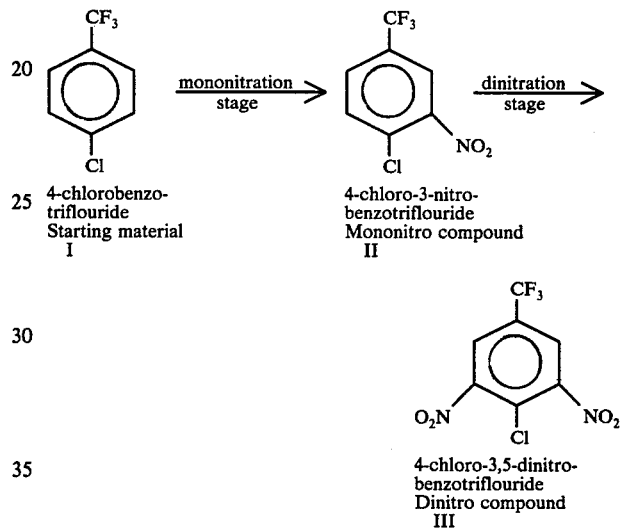

4-chlorobenzotriflouride
Starting material
I 4-chloro-3-nitro-benzotriflouride
Mononitro compound
II 4-chloro-3,5-dinitro-benzotriflouride
Dinitro compound
III Referring to the FIGURE, the process is carried out in reaction vessels 1 and 2, provided respectively for the mononitration and dinitration stages. The vessels are equipped with stirrers 3 and 4 and heating means 5 and 6, respectively.

2. Mononitration Stage

Into vessel 1 is charged 4-chlorobenzotrifluoride I and an acid mixture of nitric acid, sulfur trioxide and sulfuric acid. The sulfuric trioxide and sulfuric acid usually are combined as forming sulfuric acid or oleum. The molar ratio of nitric acid in the mixture to I suitably is at least 1:1, and, preferably, a slight excess of nitric acid over the 1:1 ratio is present, usually about 5–10%, i.e., a ratio of about 1.1:1, thereby ensuring substantially complete mononitration of I into II.

The molar ratio of nitric acid to sulfur trioxide in the acid mixture also suitably is at least 1:1. Thus, as mononitration proceeds, wherein one mole of nitric acid is consumed per mole of I, usually in less than an hour, and one mole of water is produced, the liberated water is absorbed entirely by a mole of sulfur trioxide, forming additional sulfuric acid. The ratio of nitric acid to sulfur trioxide in the acid mixture thus remains constant during the course of the mononitration.

The concentration of the respective acid components of the acid mixture is not critical; however, usually nitric acid is present at a concentration of about 8–22% by weight of the total acid mixture, and sulfur trioxide constitutes 10–27% by weight. The sulfuric acid component, obtained by difference, is about 51-82% by weight of the mixture.

The mononitration reaction is run at a temperature suitably from about 20°-80° C., and, preferably from about 50°-55° C.

At the conclusion of mononitration, there remains essentially no I and very little nitric acid or sulfur trioxide. The reaction product consists of an organic layer, which is the mononitro compound II, and a used acid layer, which is essentially sulfuric acid containing a small amount of II.

3. Dilution Step

At this point in the process, the used acid layer is diluted with water until the acid concentration is reduced to about 80-90%, and, preferably, 85%. The solubility of II in dilute acid is less than in concentrated acid; thus, any II previously dissolved in the concentrated acid layer is extracted into the organic layer. The dilute acid layer then is separated from the organic layer and discarded.

The organic layer consists of II (and III, as will be described hereinafter), which are unaffected by the dilute acid. However, any residual I, if present in the organic layer due to incomplete conversion of I into II during mononitration, is readily hydrolyzed to 4-chlorobenzoic acid. Therefore, substantially complete mononitration is important to avoid formation of this undesirable by-product.

4. Dinitration Stage

The mononitro compound then is fed as stream 8 into vessel 2 for dinitration with fresh mixed acid 9, which is also made up of nitric acid, sulfur trioxide and sulfuric acid. However, suitably the ratio of nitric acid in the fresh acid mixture to II is at least 2:1, and, preferably, at least 2.5:1, although any large excess of nitric acid may be used. The excess nitric acid present is sufficient to carry out the dinitration stage, and to provide the requisite amount of nitric acid for subsequent mononitrations. The molar ratio of nitric acid to sulfur trioxide suitably also is at least 1:1, in order to absorb water during dinitration.

The concentrations of the respective acid components of the fresh acid mixture suitably are about 18-25% by weight nitric acid, 23-32% oleum and 43-59% sulfuric acid. Preferred concentrations are 20%, 26% and 54%, respectively.

The reaction temperature for dinitration suitably is about 70°-125° C., and, preferably about 90° C. The reaction period usually is about 24 hours or less.

At the conclusion of the dinitration reaction, two layers are formed, namely, a dinitro organic layer III, and, a partially spent acid layer, which contains up to 15% of the total dinitro product. The organic layer is separated and recovered dinitro product 10. The partially spent acid layer, containing dissolved dinitro, is recycled back to the mononitration stage as recycle acid stream 11.

7. The Mononitration Stage in the Cyclic Process

Recycle acid stream 11 contains sufficient nitric acid, sulfur trioxide and sulfuric acid to effect the complete conversion of a new charge of I into II. Subsequent dilution of the used acid mixture extracts both the dissolved mononitro II and the dinitro compounds III into the organic layer; therefore both are carried forward to subsequent dinitration stages to increase the overall yield of the desired dinitro product in that stage.

8. The Dinitration Stage in the Cyclic Process

Upon carrying forward of the organic layer produced above, and effecting dinitration in the cyclic mode, a yield of the desired 4-chloro-3,5-dinitrobenzotrifluoride III of at least 94.7% is obtained in the cyclic process.

9. Working Examples

1. Preparation of 4-Chloro-3,5-Dinitrobenzotrifluoride

Into a 1-liter, 4-necked flask 1 equipped with a stirrer, condenser, thermometer and dipping funnel, is charged 330g. of a mixed acid comprising 20% by weight nitric acid, 26% sulfur trioxide and 54% sulfuric acid, which is 1:1 mole ratio of nitric acid to oleum. The mixed acid is heated to 50°-55° C. and 4-chlorobenzotrifluoride (180.5 g., one mole), a 1:1 molar ratio of nitric acid to 4-chlorobenzotrifluoride, is added with cooling in ½ hr. at 50°-55° C. Gas chromotographic analysis indicated a complete conversion of the starting material to 4-chloro-3-nitrobenzotrifluoride.

The used acid mixture then is diluted with 50 ml. of water at 50°-52° C. with cooling during 15 minutes to form an 85% by weight sulfuric acid solution. The dilute used acid which contains less than 0.1% organics and about 1% nitric acid, then is separated from the mononitro product and discarded. The recovered mononitro oil weighs 225g. (one mole).

The mononitro oil then is added during 5 min. to a similarly equipped reaction vessel 2 charged with 786.0g. of fresh mixed acid containing 20% nitric acid, 26% oleum and 54% sulfuric acid, a 2.5:1 molar ratio of nitric acid to sulfur trioxide, which is heated to 50°-55° C. The reaction mixture then is heated further to 90° C in 20 min. and is maintained at 90° C. for 20 hrs. At the end of this period gas chromotographic analysis indicated a greater than 99.2% conversion to 4-chloro-3,5-dinitrobenzotrifluoride of 96.5% purity. The lower phase partially spent acid layer (770g.), which contains about 25g. dinitro compound is separated at 80° C. for recycling. The upper phase dinitro oil weighs up to 256g. (94.8% of theoretical, based upon the 4-chlorobenzotrifluoride starting material), and solidifies upon cooling to 55°-57° C.

2. Preparation of 4-chloro-3,5-Dinitrobenzotrifluroide in Cyclic Process

Charged to flask 1 is the recovered partially spent acid above (770g) at 50°-55° C., and a new batch of 4-chlorobenzotrifluoride (180.5g., one mole) is added with cooling in ½ hr. at 50°-55° C. Gas chromotographic analysis indicated a total conversion to the mononitro compound. The used acid then is diluted to 85% sulfuric acid with 120 ml. of water at 50°-52° C. with cooling in about 15 min. The dilute used acid then is separated from the mononitro product. The recovered mononitro oil weighs 250g. and contains 25g. dinitro oil. The mixture of mononitro and dinitro oils is carried froward as the charge to be further nitrated in flask 2 using fresh mixed acid. The dinitro component of this mixture provides additional yield, to be separated in this stage as the upper phase dinitro oil.

While the invention has been described with particular reference to certain embodiments thereof, it will be understood that certain changes and modifications may be made which are within the skill of the art.

Therefore, it is intended to be bound by the appended claims only, in which what is claimed is:

1. A cyclic, two-stage nitration process for preparing 4-chloro-3,5-dinitrobenzotrifluoride from 4-chlorobenzotrifluoride in high yield which comprises:
    (a) mononitrating 4-chlorobenzotrifluoride substantially completely to 4-chloro-3-nitrobenzotrifluoride with acid mixture of nitric acid, sulfur trioxide and sulfuric acid,
    (b) diluting the used acid mixture with water to form a dilute used acid layer and 4-chloro-3-nitrobenzotrifluoride organic layer,
    (c) separating said dilute used acid layer from said organic layer,
    (d) dinitrating said 4-chloro-3-nitrobenzotrifluoride organic layer with a fresh acid mixture of nitric acid, sulfur trioxide, and sulfuric acid to form 4-chloro-3,5-dinitrobenzotrifluoride product, and a partially spent acid mixture containing a portion of said product dissolved therein, said fresh acid mixture containing sufficient nitric acid to effect said nitration and to provide for said mononitration upon recycling of said partially spent acid mixture back to step (a),
    (e) separating said 4-chloro-3,5-dinitrobenzotrifluoride product from said partially spent acid mixture, and,
    (f) recycling said partially spent acid mixture back to step (a).

2. A process according to claim 1 wherein step (a) is carried out with an acid mixture having at least a 1:1 molar ratio of nitric acid to 4-chlorobenzotrifluoride.

3. A process according to claim 2 wherein step (a) is carried out with an acid mixture in which the molar ratio of nitric acid to sulfur trioxide is at least 1:1.

4. A process according to claim 3 wherein the concentration of nitric acid, sulfur trioxide and sulfuric acid in said acid mixture is about 8–22%, 10–27%, and 51–82% by weight, respectively.

5. A process according to claim 4 wherein the reaction temperature of step (a) is about 20°–80° C.

6. A process according to claim 5 wherein said temperature is about 50°–55° C.

7. A process according to claim 1 wherein step (b) is carried out to form dilute used acid layer of 80–90% by weight acid.

8. A process according to claim 1 wherein step (d) is carried out with an acid mixture having at least a 2:1 molar ratio of nitric acid to 4-chloro-3-nitrobenzotrifluoride.

9. A process according to claim 8 wherein said molar ratio is at least 2.5:1.

10. A process according to claim 1 wherein step (d) is carried out with an acid mixture in which the molar ratio of nitric acid to sulfur trioxide is at least 1:1.

11. A process according to claim 10 wherein the concentration of nitric acid, sulfur trioxide and sulfuric acid is about 18–25% and 43–59% by weight, respectively.

12. A process according to claim 11 wherein said concentration is about 20%, 26% and 54%, respectively.

13. A process according to claim 1 wherein the reaction temperature in step (d) is about 70°–125° C.

14. A process according to claim 13 wherein said temperature is about 90° C.